(12) United States Patent
Chang et al.

(10) Patent No.: US 9,925,201 B2
(45) Date of Patent: *Mar. 27, 2018

(54) COMPOSITIONS AND TREATMENT FOR EYE DISEASES AND DISORDERS

(71) Applicant: GLIA, LLC, Boston, MA (US)

(72) Inventors: Wei-Wei Chang, Boston, MA (US); Kenneth Sawyer, Cushing, ME (US)

(73) Assignee: GLIA, LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/380,741

(22) Filed: Dec. 15, 2016

(65) Prior Publication Data

US 2017/0189413 A1    Jul. 6, 2017

Related U.S. Application Data

(63) Continuation of application No. 14/417,640, filed as application No. PCT/US2013/052264 on Jul. 26, 2013, now abandoned.

(60) Provisional application No. 61/676,530, filed on Jul. 27, 2012, provisional application No. 61/756,321, filed on Jan. 24, 2013.

(51) Int. Cl.
A61K 31/57    (2006.01)
A61K 9/00     (2006.01)

(52) U.S. Cl.
CPC ............ *A61K 31/57* (2013.01); *A61K 9/0014* (2013.01); *A61K 9/0048* (2013.01)

(58) Field of Classification Search
None
See application file for complete search history.

(56) References Cited

U.S. PATENT DOCUMENTS

2010/0016264 A1    1/2010    Connor et al.
2012/0028910 A1    2/2012    Combal et al.

FOREIGN PATENT DOCUMENTS

WO    WO 2004/066967    8/2004
WO    WO 2008/070726    6/2008
WO    WO 2008/070728    6/2008
WO    WO 2011/039638    4/2011

*Primary Examiner* — Samantha Shterengarts
(74) *Attorney, Agent, or Firm* — Cesari and McKenna, LLP

(57) ABSTRACT

The invention relates to compositions and methods for treating eye diseases and disorders. More specifically, the invention provides compositions comprising progesterone and methods of treating ocular surface diseases and disorders comprising applying such compositions topically.

14 Claims, No Drawings

COMPOSITIONS AND TREATMENT FOR EYE DISEASES AND DISORDERS

CROSS REFERENCE TO RELATED APPLICATIONS

This application is a continuation of U.S. patent application Ser. No. 14/417,640, filed on Jan. 27, 2015, which is the national stage of International Application PCT/US2013/052264, filed on Jul. 26, 2013, which claims priority to U.S. Provisional Applications 61/756,321, filed on Jan. 24, 2013, and 61/676,530, filed on Jul. 27, 2012. The content of these prior applications is hereby incorporated by reference herein in its entirety.

TECHNICAL FIELD OF THE INVENTION

The invention relates to compositions and methods for treating eye diseases and disorders. More specifically, the invention provides compositions comprising progesterone and methods of treating ocular surface diseases and disorders comprising applying such compositions topically.

BACKGROUND OF THE INVENTION

Tears protect the eyes from many kinds of external stimuli. It is estimated that over 30% of people suffer from some type of ocular surface disease or disorder, many being classified as suffering from dry eye syndrome (DES) or keratoconjunctivitis sicca (KCS). DES refers to an ocular affliction characterized by a dryness sensation in the eye often accompanied by grittiness, tearing, burning, blurred vision, or a foreign-body sensation. If left untreated, dry eyes can lead to more serious problems such as chronic dry eye syndrome, inflammation of the ocular surface and epithelial cell damage, or even blindness. It is generally accepted that dry eyes are caused by an abnormality in the quality or quantity of tears on the eye surface, such as tear imbalance, that could lead to a loss of proper lubrication and discomfort. The cause of these abnormalities can be an underlying medical condition such as Sjögren's syndrome, vitamin deficiencies such as vitamin A, rheumatoid arthritis, lupus, ocular rosacea, or other non-specific autoimmune or inflammatory disease. Other causes include bacterial infections of the eye, post-refractive surgery disruptions, allergic reactions, contact lens wearing, lid or blink anatomy abnormalities, neurological damage, and side effects from certain medications.

The tear film consists of three layers: the outer lipid layer, the middle aqueous layer, and the inner mucus layer. The lipid layer consists of oils exuded from over 20 meibomian glands that line the inner edge of the eyelid. The lipid layer is in contact with the air and functions to inhibit evaporation of tears. The middle layer is the aqueous layer and is produced by the lacrimal gland located above the upper outer portion of the globe within the orbit. The aqueous layer contains ions and macromolecules such as proteins. The mucus layer is between the aqueous layer and the ocular epithelial cells and is formed by the goblet cells located in the subconjunctival space. The primary function of the mucus layer is to help stabilize the tear film.

Aqueous tears are produced by the lacrimal glands and the conjunctiva, and those that remain in the eye can be evaporated or drained through the lacrimal canaliculi into the nose. A reduction in tear production or increase in tear elimination will often lead to dry eye. In addition, the lipid layer and the mucus layer play important roles in the dynamics of aqueous tears. For example, imperfections of the lipid layer can increase tear evaporation rates, and insufficient production of mucus can destabilize the tear film and lead to tear film disruption.

Dry eye syndrome has numerous causes typically associated with a deficiency in one or more layers of the tear film. In addition to the underlying diseases mentioned above, changes in steroid hormone levels have been implicated in causing dry eye syndrome. For example, dry eye is associated with the decline in estrogen, progesterone and testosterone levels in post-menopausal women. Furthermore, men on anti-androgen therapies for disorders such as hormone-dependent prostate cancer often suffer from dry eye (Krenzer et al., (2000) *J Clin Endocrin & Metab*, 85 (12): 4874-82.) Multiple studies on both human and rodent ocular gland tissues suggest the presence of estrogen, progesterone and androgen receptor mRNA and proteins in multiple ocular tissues including the lacrimal gland, lacrimal gland acinar epithelial cells, and meibomian gland. As described in U.S. Pat. No. 6,659,985, and US Patent Application Publications 200810132475 and 201010016264, topical therapies comprising the application of testosterone, estrogen, and/or progesterone directly to the eye or proximately to the eye have shown some efficacy in improving the symptoms of dry eye. Topical administration of these compositions in or near the eye can, however, cause further irritation, burning, or stinging in the eye, and the concentrations of the hormones used in these treatment methods are high enough such that systemic hormone exposure may be a concern.

Aqueous tear deficiency (ATD) is the most common cause of dry eye and is due to insufficient tear production from the lacrimal glands. Aqueous secretion from the lacrimal gland is generally controlled by the ophthalmic division of the trigeminal $V_1$ nerve. This network of nerve fibers directly and indirectly controls tear formation in the lacrimal glands resulting from both reflexive responses such as a foreign body entering the eye and emotional responses. Structurally, these nerve fibers lie proximate to the surface of the skin, for example, at the forehead, temples, and the area just below the eyebrow.

SUMMARY OF THE INVENTION

The inventors surprisingly found that progesterone, applied topically in low doses to the regions of the face outside of the palpebral part of the eye, improves symptoms of ocular surface diseases or disorders, including dry eye.

In one aspect, the invention provides a method for treating ocular surface diseases or disorders in a patient comprising topically administering to a patient in need thereof a pharmaceutical composition comprising an effective amount of progesterone and one or more pharmaceutically acceptable excipients, wherein the composition is applied to one or more regions of the face that are outside of the palpebral part of the eye.

In another aspect, the invention provides a pharmaceutical composition for topical administration comprising a therapeutically effective amount of progesterone and one or more pharmaceutically acceptable excipients, wherein the composition is suitable for application to the regions of the face that are outside of the palpebral part of the eye of a patient.

DETAILED DESCRIPTION OF THE INVENTION

The present invention provides methods for treating ocular surface diseases or disorders and topical pharmaceutical compositions comprising an effective amount of progesterone and one or more pharmaceutically acceptable carriers or excipients. Although many topical compositions comprising progesterone exist, compositions that have advantageous properties such as enhanced penetration of progesterone into the skin, limited systemic exposure of progesterone, and good stability and/or increased acceptance by the patient are highly desirable. Hence, it is a general object of the present invention to provide compositions that possess such desirable properties, and these objectives are achieved by providing the compositions as defined herein.

In addition to natural progesterone, many synthetic hormones that mimic progesterone have been developed. As used herein, the term "progestagens" refers to natural or synthetic progesterone, synthetic hormones that mimic progesterone such as progestin, medroxyprogesterone acetate (medrysone), norethindrone or norethisterone, norethindrone acetate, megestrol acetate, 17-a-hydroxyprogesterone caproate, or norgestrel, or a derivative or prodrug thereof. In certain embodiments of the present invention, natural progesterone is preferred. In other embodiments of the present invention, a synthetic hormone that mimics progesterone is preferred. Natural progesterone can be derived from multiple sources and presented in multiple forms. Commercial sources of natural progesterone include soy, wild yam, and other plant-based sources. The U.S. Pharmacopoeia recognizes natural progesterone in three forms, namely progesterone USP micronized, progesterone USP wettable microcrystalline, and progesterone USP milled. In one embodiment, the progesterone is derived from wild yam. In another embodiment, the progesterone is wettable microcrystalline. In a preferred embodiment, the progesterone is progesterone USP wettable crystalline derived from wild yam.

The composition of the present invention comprises one or more pharmaceutically acceptable carriers or excipients suitable for use in topical pharmaceutical formulations. Such excipients can facilitate the processing or delivery of the progesterone to the application site and proper formulation can be dependent on the desired application process. Non-limiting exemplary formulations are provided below.

The topical formulations useful in the present invention can be made into a variety of product types or forms. These include liquids, lotions, creams, gels, sticks, sprays, ointments, pastes, mousses, cosmetics and films. These product types can include one or more carrier systems such as solutions, emulsions, suspensions, gels, solids, or even liposomes or other microspheres. Techniques for formulation of topical product types are well known in the art. The formulation chosen can be selected to enhance delivery of the progesterone as well as provide other desired characteristics such as emollience or color. Other formulations useful in the present invention can be designed as transdermal devices (patches).

Transdermal patches can be of any suitable patch structure, including single or multi-layer drug-in-adhesive, matrix, reservoir, or vapor patches. Construction of such patch structures are well known in the art and include patches that typically contain a therapeutically effective component or drug, one or more adhesives, one or more membranes, a backing, and a protective liner that is often removed prior to use. In a method of the present invention, the transdermal patch can be placed on the surface of the skin to one or more of the regions of the face that are outside of the palpebral part of the eye. The patch can be applied every day, or on longer intervals such as once every two days, once a week, or once a month.

Lotions are preparations to be applied to the surface of the skin and tend to be liquid or semi-liquid. Lotions can be formulated with an aqueous or oily base and in general further comprise one or more emulsifying agents, stabilizing agents, suspending agents, solubilizing agents, thickening agents, preservatives, or coloring agents.

Creams containing progesterone are typically more viscous than lotions and can be semi-solid emulsions such as oil-in-water or water-in-oil. Cream bases generally contain one or more oils, emulsifiers, and aqueous components. Many oils are suitable for cream formulations and may include animal or vegetable oils, waxes and fatty acids or alcohols, amides and esters thereof. The aqueous component can include components in addition to water, such as alcohols, polyols, humectants, viscosity builders and preservatives. Emulsifiers typically include nonionic, anionic, cationic, or amphoteric surfactants.

Gel formulations may also be suitable for the present invention. Gels are generally viscous, semi-solid systems containing one or more types of macromolecules distributed relatively uniformly throughout a carrier liquid. Such carrier liquid can be aqueous, but may also contain solvents or co-solvents, or other pharmaceutically acceptable excipients.

Ointments suitable for the present invention are homogeneous, viscous, semi-solid preparations, most commonly greasy, thick oils (oil 80%—water 20%) with a high viscosity. Ointments are generally used as emollients or for the application of active ingredients to the skin where a degree of occlusion is desired. The base of the ointment can be petrolatum, paraffin, microcrystalline wax, ceresine, absorption bases such as wool fat or beeswax, water soluble bases, emulsifying wax, cetrimide, or vegetable oils such as olive oil, coconut oil, sesame oil, almond oil or peanut oil.

Formulations that are solid stick or soft solid when at ambient room temperature of about 25° C. can be suitable for the present invention. The stick form is an example of a solid form, and the soft solid is a thickened form that may or may not actually be solid. The stick form can be distinguished from a soft solid in that, in a stick, the formulated product can retain its shape for extended time periods outside the package, the product not losing its shape significantly (allowing for some shrinkage due to evaporation). Adjustment of amounts of gelling or thickening agents can be used in order to form a soft solid or stick.

Soft solids can be suitably packaged in containers that have the appearance of a stick, but which dispense through apertures (for example, slots or pores) on the top surface of the package. The soft solid products have also been called soft sticks or "smooth-ons," and hereinafter are generically called "soft solids." Reference is made to U.S. Pat. No. 5,102,656, U.S. Pat. No. 5,069,897, and U.S. Pat. No. 4,937,069, and such patents are herein incorporated by reference to the extent that they teach soft solids.

Various formulations of the present invention can include pharmaceutically acceptable excipients to alter or enhance properties of the composition such as viscosity, scent, texture, pH and coloring, or may enhance properties of the active ingredient such as solubility or absorption of the natural progesterone.

Pharmaceutical excipients useful in the present invention include viscosity enhancers such as cellulose or polyvinyl based polymers, including hydroxyethylcellulose, hydroxypropylmethylcellulose, methylcellulose, hyaluronic acid, carbomers, polyvinyl alcohols, and polyvinylpyrrolidones. Additional useful excipients can include texture enhancing components and solvents or co-solvents such as glycerol, propylene glycol, and other alcohols such as isopropanol or ethanol.

The compositions of the present invention can also further comprise buffers or simple buffering systems for achieving or maintaining a particular pH or pH range. Such buffers and buffering systems are generally known to those skilled in the art and include acetate, phosphate and/or citrate buffers.

The compositions may further comprise one or more pharmaceutically acceptable preservatives including antimicrobials such as benzoic and ascorbic acids and their salts, and phenolic compounds such as methyl, ethyl, propyl and butyl p-hydroxybenzoate (parabens), quaternary ammonium salts, alcohols, phenols, mercurials and biguanides, and antioxidants such as alky gallates, butylated hydroxyanisole, butylated hydroxytoluene, nordihydroguaiaretic acid and tocopherols, ascorbic acid, the potassium and sodium salts of sulphurous acid, citric acid, editic acid and its salts, lecithin and tartaric acid.

Compositions of the present invention comprise a therapeutically effective amount of progesterone. A therapeutically effective amount of progesterone is that amount that achieves the desired therapeutic response of reducing or eliminating one or, more symptoms of an ocular surface disease or disorder when administered according to single or multiple dosing regimens. It will be understood, however, that the total daily usage of the composition of the present invention will be decided by the attending physician within the scope of sound medical judgment. In determining the therapeutically effective amount or dose of progesterone, a number of factors can be considered including, but not limited to, the species of the patient to be treated, its weight, age, gender and general condition, the dosing regime, the patient's use of concomitant medications, the severity of the disorder to be treated, and other relevant circumstances understood by those skilled in the art. A therapeutically effective amount of progesterone may vary over a wide range. In one embodiment, a therapeutically effective amount is from about 0.05 mg to about 5.0 mg per dose or application. In another embodiment, a therapeutically effective amount of progesterone is from about 0.1 mg to about 3.25 mg per dose or application.

The composition of the present invention can be formulated into one or more topical formulations containing from about 0.01% to about 10% progesterone w/w of the total formulation. In a preferred embodiment, the amount of progesterone in the formulation is from about 0.025% to about 5.0%. In another preferred embodiment, the amount of progesterone in the formulation is from about 0.05% to about 4.0%. In another embodiment, the amount of progesterone in the formulation is from about 0.1% to about 2.0%. In particular embodiments, the amount of progesterone in the formulation is selected from about 0.1%, about 0.25%, about 0.5%, about 1.0%, about 1.5%, and about 2.0%.

The composition of the present invention can also be used in combination with one or more additional therapies for treating an ocular surface disease or disorder or managing the symptoms thereof. For example, the composition of the present invention can be used in combination with therapies such as moisturizing drops or artificial tears, punctal plugs, prostaglandin analogs, beta blockers, alpha agonists, carbonic anhydrase inhibitors, steroids, and antibiotics. Such therapies can be administered simultaneously with the composition of the present invention, or proximately or remotely in time.

As used herein, the term "patient" means a mammal, including humans, companion animals such as dogs, cats and rabbits, and other domesticated or non-domesticated animals including cattle, sheep, and various other farm animals. In one embodiment, the patient is a human. In another embodiment, the patient is a companion animal.

The composition of the present invention can be applied topically to the face to the regions that are outside of the palpebral part of the eye. The palpebral part of the eye refers to the region of and around the eye associated with the palpebral component of the orbicularis oculi muscle group. The palpebral component of the muscles originates in the palpebral ligament and runs above and below the eye to the lateral angle of the eye, forming concentric circles around the eye. The palpebral part of the eye for purposes of the present invention thus refers to the facial surface around the eye that corresponds to the location of the palpebral component of the orbicularis oculi muscle lying underneath the facial skin. Non-limiting examples of these regions include, for example, the forehead above the eyebrows, the temple area between the end of the eyebrow and the hairline including the temple region, the upper cheek, or the sides or bridge of the nose. In one embodiment, the composition of the present invention is applied to the forehead. In another embodiment, the composition is applied to one or both temple regions. In a further embodiment, the composition is applied to the upper cheek. In another embodiment, the composition is applied to one or both sides or the bridge of the nose. In one embodiment, the composition is applied to two or more regions of the face simultaneously or sequentially, and proximately or distant in time. For example, the composition can be applied to the forehead, and further applied to the temple region at the same time or at the next prescribed time, whether such next prescribed time is the same day or a different day. In one embodiment, the composition is applied to the same region of the face each time it is applied. In a further embodiment, the composition can be applied intranasally to the mucous membrane inside of the nose.

The composition of the present invention can be applied at least once a day. In some embodiments, the composition is applied at least once a day, or twice a day, or three times a day, or four times a day, or up to four times per day. The composition can be applied every day, every other day, every third day, or as often as needed to relieve the symptoms of the ocular surface disease or disorder that the patient suffers from. It is understood that the present invention includes dosing regimens that include structured regimens such as once, twice, three or four times a day every day, as well as dosing regimens that are once a day every other day or that are on an "as needed" basis. The exact dosing regimen can be tailored specifically for each patient and is determined by the attending physician or practitioner based on the needs of the patient and various other parameters understood by those skilled in the art.

Not being bound by any particular theory, it is believed that the topical application of progesterone to an area of the skin such as the forehead, upper cheek, nose or temples is in an area that is proximal to the location of the trigeminal $V_1$ nerve branch. Progesterone has been associated with analgesic and neuroprotective effects in models of neuropathy and may, therefore, play a role in the control of tear production in the lacrimal gland.

The progesterone may directly or indirectly stimulate the nerve fibers such that the lacrimal gland is stimulated and increases the amount of tears it produces and/or secretes into the eye. Such increase in tear production and/or secretion provides relief from common symptoms of ocular surface diseases or disorders including dry eye and does not cause the irritation to the eye that can be caused by the direct application of alternative therapies to the eye or near the eye.

In the method of the present invention, the ocular surface disease or disorder to be treated can be caused by any one or more events or conditions leading to symptoms of eye dryness and/or discomfort. Non-limiting examples of such events or conditions may be selected from mild to moderate mechanical or thermal trauma to the eye, Sjögren's syndrome, rheumatoid arthritis, lupus, ocular rosacea, other non-specific autoimmune or inflammatory diseases, bacterial infections of the eye, post-refractive surgery disruptions, allergic reactions, contact lens wearing, lid or blink anatomy abnormalities, neurological damage, environmental conditions, eye strain, side effects from certain medications such as chemotherapy or other medications that typically cause xerostomia, and combinations thereof.

The method of the present invention further provides treatment for, reduction of, or prevention of symptoms associated with an ocular surface disease or disorder. Symptoms can include one or more of the following: inadequate tear production, general eye discomfort, pain, soreness or stinging, increased pressure, grittiness, redness, decreased acuity, excessive mucus discharge, photosensitivity, itchiness, and waking during sleep due to eye discomfort. Treatment, reduction, or prevention of these or other symptoms of ocular surface diseases or disorders is often referred to as "relief" from such symptoms.

Pharmaceutical Formulations for Topical Administration

Exemplary formulations for use in the methods of the invention may be prepared as indicated below. These exemplary formulations are provided for the purpose of illustrating the invention and should not be construed as limiting.

Batch quantities of topical formulations can be prepared by mixing carbomer 940 and water until completely stirred and desired viscosity is obtained, approximately one to two hours. Sodium hydroxide dissolved in water is added to the carbomer mixture. Glycerin is heated and one or more parabens are added to the heated glycerin. The glycerin mixture and the carbomer mixture can be combined to complete the base. Wettable progesterone in an amount sufficient to reach the desired concentration is added to the base mixture and mixed thoroughly. Alternatively, the wettable progesterone can be added to the heated glycerin and parabens solution.

| Formulation 1 | | |
| --- | --- | --- |
| | Grams | % total formulation (w/w) |
| BASE | | |
| Glycerin | 12.062 | 7.45% |
| Methylparaben | 0.313 | 0.19% |
| Propylparaben | 0.04 | 0.02% |
| Sodium Hydroxide | 0.993 | 0.61% |
| Water, purified | 22.1 | 13.64% |
| Carbomer 940 | 2.01 | 1.2% |
| Water, purified | 122.89 | 75.85% |
| | 160.408 | 99.01% |
| Progesterone, wettable | 1.6 | 1.0% |
| TOTAL | 162.008 | 100% |

| Formulation 2 | | |
| --- | --- | --- |
| BASE | Grams | % total formulation (w/w) |
| Glycerin | 12.0 | 7.6% |
| Methylparaben | 0.3 | 0.2% |
| Propylparaben | 0.04 | <0.1% |
| Sodium Hydroxide | 1.0 | 0.6% |
| Water, purified | 20.0 | 12.7% |
| Carbomer 940 | 1.75 | 1.1% |
| Water, purified | 123.0 | 77.8% |
| | 158.09 | 100% |
| BASE (g) | Progesterone, wettable (g) | Final concentration (% P) |
| 64.5 | 0.645 | 1.0% |
| 64.5 | 2.58 | 4.0% |

Batch quantities of topical formulations can be prepared by mixing carbomer 940 and water until completely stirred and desired viscosity is obtained, approximately one to two hours. Sodium hydroxide is dissolved in water for about 10-15 minutes. The glycerin is heated to 60° C. and isopropyl alcohol, parabens and progesterone wettable are added to the heated glycerin and mixed until relative uniform consistency is achieved. The carbomer and the glycerin mixture are combined and mixed well. The sodium hydroxide in water is added to the carbomer-glycerin mixture and is mixed well. Final pH is determined to be in the range of about 6.0 to about 6.5.

| Formulation 3 | | |
| --- | --- | --- |
| | Grams | % total formulation (w/w) |
| Carbomer 940 | 1.2 | 1.2% |
| Water, purified | 78.0 | 77.3% |
| Sodium Hydroxide | 0.5 | 0.5% |
| Water, purified | 8.0 | 7.9% |
| Glycerin | 7.0 | 6.9% |
| Isopropyl Alcohol | 5.0 | 5.0% |
| Methylparaben | 0.15 | 0.15% |
| Propylparaben | 0.02 | 0.02% |
| Progesterone wettable | 1.0 | 1.0% |
| TOTAL | 100.87 g | 100% |

EXAMPLES

Example 1

Four females age 25-45, twelve females over the age of 45, and two males over the age of 45 were treated with 1% (n=17) or 4% (n=1) topical progesterone compositions the same as or similar to the formulations described above. Fifteen of the eighteen patients completed a McMonnies Dry Eye questionnaire and all eighteen reported one or more symptoms of dry eye disorder prior to treatment. McMonnies scores for all patients that completed the questionnaire ranged from 9-28 with an average score of 16.0. Generally, McMonnies scores over 20 indicate dry eye disorder whereas scores between 10 and 20 are generally suggestive of borderline dry eye.

All patients treated with 1% or 4% progesterone compositions reported some relief from the symptoms or discomfort each experienced prior to treatment. Many patients that had a history of chronic usage of over-the-counter lubricating eye drops reported their ability to reduce or eliminate the use of such drops following treatment.

Example 2

Single Treatment Tear Breakup Time (TBUT).

Six patients were observed for changes in TBUT following a single administration of 1% progesterone composition. Prior to treatment, patients complete an OSDI survey to indicate the severity of dry eye symptoms. TBUT is determined by instilling fluorescein in the eye, waiting approximately two minutes and then measuring the time lapse in seconds between a blink and the appearance of the first dry spots on the cornea. Liquid fluorescein without any anesthetic is applied with a micropipette to the inferior cul-de-sac of the right eye. After two blinks, the tear film is examined using the broad-beam of a slit lamp with a blue filter. Time is measured until the first dry spots appear on the cornea. Following a single instillation of fluorescein, TBUT is measured up to three times in succession, each reading beginning with the patient blinking twice followed by staring. The entire procedure is repeated in the left eye. Approximately 100-200 mg of 1% progesterone composition is applied to the forehead of each patient above the brow line. After 45-60 minutes, the TBUT procedure is repeated in both eyes. Pre-treatment and post-treatment TBUT in seconds is indicated in Table 1 for each patient. TBUT of less than 10 seconds is considered abnormal, indicative of tear instability.

TABLE 1

| | OSDI Score | | TBUT (sec) Left Eye | | | TBUT (sec) Right Eye | | | Average |
|---|---|---|---|---|---|---|---|---|---|
| Patient 1 | 58.3 | Pre tx | 7.5 | 8.9 | 4.8 | 10.9 | 16.0 | 18.4 | 11.083 |
| | | Post tx | 51.9 | 65.7 | | 55.2 | 44.2 | | 54.250 |
| Patient 2 | 4.2 | Pre tx | 27.8 | 32.6 | 36.2 | 21.0 | 35.0 | 23.0 | 29.267 |
| | | Post tx | 51.5 | 73.7 | | 62.3 | 72.3 | | 64.950 |
| Patient 3 | 62.5 | Pre tx | 6.7 | 7.0 | 7.5 | 4.2 | 5.4 | 6.1 | 6.150 |
| | | Post tx | 7.9 | 7.7 | 6.5 | 7.7 | 9.2 | 8.2 | 7.867 |
| Patient 4 | 20.8 | Pre tx | 3.3 | 2.7 | 2.6 | 3.4 | 4.1 | 3.9 | 3.333 |
| | | Post tx | 6.3 | 10.7 | 9.1 | 4.6 | 5.2 | 5.7 | 6.933 |
| Patient 5 | 52.1 | Pre tx | 8.1 | 13.1 | 13.9 | 10.3 | 9.2 | 8.2 | 10.467 |
| | | Post tx | 9.4 | 10.6 | 15.2 | 8.2 | 7.5 | 7.5 | 9.733 |
| Patient 6* | n/a | Pre tx | | | | 18.4 | 78.9 | 65.0 | 54.100 |
| | | Post tx | | | | 100.0 | | | 100.000 |

*Measurements from patient's left eye are unavailable. Right eye reading ended at 100 seconds because patient blinked prior to measurable tear break-up.

Increases in average TBUT ranged from essentially no change (−0.73 sec) to an increase of up to almost 46 seconds, with an average change of 21.56 seconds. The TBUT test showed a significant improvement even after just one treatment, with a p-value of 0.0318. Significant improvement (p-value of 0.0749) is still present even after removing the incomplete data from Patient 6.

Example 3

One patient with a history of chronic dry eye syndrome and heavy corneal staining was treated with absorbable punctal plugs, and approximately one month later began treatment with 1% progesterone. The same patient was treated approximately one year later with absorbable punctal plugs and continued treatment with 1% progesterone. The patient reported continued improvement of dry eye symptoms during the course of treatment. After approximately two years following the first punctal plug treatment, the patient reported no notable dry eye symptoms and presented little or no corneal staining.

What is claimed:

1. A method for treating ocular surface diseases or disorders in a patient comprising topically administering to a patient in need thereof a pharmaceutical composition comprising an effective amount of progesterone and one or more pharmaceutically acceptable excipients, wherein the composition is applied to the forehead or the temple region.

2. The method of claim 1, wherein the disease or disorder is dry eye syndrome.

3. The method of claim 1, wherein the progesterone is administered as a composition comprising from 0.01% to 10% w/w progesterone.

4. The method of claim 3, wherein the composition comprises from 0.1% to 2.0% w/w progesterone.

5. The method of claim 1, wherein the effective amount of progesterone is from 0.05 mg to 5.0 mg.

6. The method of claim 1, wherein the patient is a human.

7. The method of claim 1, wherein the patient is a companion animal.

8. The method of claim 1, wherein the ocular surface disease or disorder is mild to moderate mechanical or thermal trauma to the eye, Sjögren's syndrome, rheumatoid arthritis, lupus, ocular rosacea, other non-specific autoimmune or inflammatory diseases, bacterial infections of the eye, post-refractive surgery disruption, allergic reactions, lid or blink anatomy abnormalities, neurological damage, environmental conditions, eye strain, side effects from medications, or a combination thereof.

9. The method of claim 8, wherein the progesterone is administered as a composition comprising from 0.01% to 10% w/w progesterone.

10. The method of claim 8, wherein the patient is a human.

11. The method of claim 8, wherein the patient is a companion animal.

12. The method of claim 8, wherein the ocular surface disease or disorder is Sjögren's syndrome.

13. The method of claim 8, wherein the ocular surface disease or disorder is post-refractive surgery disruption.

14. The method of claim 8, wherein the ocular surface disease or disorder is ocular rosacea.

* * * * *